United States Patent
Bilby et al.

(10) Patent No.: US 12,259,357 B2
(45) Date of Patent: Mar. 25, 2025

(54) ELECTROCHEMICAL EXHAUST GAS SENSOR WITH PHOTOLYSIS

(71) Applicant: Ford Global Technologies, LLC, Dearborn, MI (US)

(72) Inventors: David Bilby, Royal Oak, MI (US); Reinoud Felix Wolffenbuttel, Leidschendam (NL)

(73) Assignee: Ford Global Technologies, LLC, Dearborn, MI (US)

( * ) Notice: Subject to any disclaimer, the term of this patent is extended or adjusted under 35 U.S.C. 154(b) by 456 days.

(21) Appl. No.: 17/724,909

(22) Filed: Apr. 20, 2022

(65) Prior Publication Data
US 2023/0341352 A1    Oct. 26, 2023

(51) Int. Cl.
| | |
|---|---|
| *G01N 27/49* | (2006.01) |
| *G01N 27/404* | (2006.01) |
| *G01N 27/407* | (2006.01) |
| *G01N 33/00* | (2006.01) |

(52) U.S. Cl.
CPC ......... *G01N 27/49* (2013.01); *G01N 27/4045* (2013.01); *G01N 27/4073* (2013.01); *G01N 33/0037* (2013.01); *G01N 33/0047* (2013.01)

(58) Field of Classification Search
CPC .. G01N 27/49; G01N 27/4073; G01N 27/407; G01N 27/404; G01N 27/4045; G01N 33/0037; G01N 33/0047
See application file for complete search history.

(56) References Cited

U.S. PATENT DOCUMENTS

| | | | |
|---|---|---|---|
| 3,881,111 A | 4/1975 | Stephens et al. | |
| 6,051,436 A * | 4/2000 | Reagen | G01N 33/188 |
| | | | 436/107 |
| 6,065,327 A * | 5/2000 | Fukaya | G01N 27/407 |
| | | | 73/23.32 |
| 2009/0137055 A1 | 5/2009 | Bognar | |

FOREIGN PATENT DOCUMENTS

| | | |
|---|---|---|
| CN | 109975231 | 7/2019 |
| JP | 4543186 | 9/2010 |
| JP | 5003976 | 8/2012 |

OTHER PUBLICATIONS

Fahnebrock et al., "A solid electrolyte sensor as an alarm device to detect chlorinated hydrocarbons in exhaust gas," Sensors and Actuators B, 18-19 (1994) 515-517 (Year: 1994).*
Jimenez, Lecture 7: Photochemistry of Important Atmospheric Species, Power Point Presentation for Atmospheric Chemistry CHEM-5151 / ATOC-5151, Spring 2005, 17 pages.
Nist National Institute of Standards and Technology, U.S. Department of Commerce, NIST Chemistry WebBook, SRD69, 2023, available at URL https://webbook.nist.gov/chemistry/.

* cited by examiner

Primary Examiner — Alexander S Noguerola
(74) Attorney, Agent, or Firm — Burris Law, PLLC

(57) ABSTRACT

An automotive exhaust gas sensor includes a gas chamber, an ultraviolet light source configured to emit ultraviolet light into the gas chamber and to photolyze an exhaust gas sample in the gas chamber, and an electrochemical detector disposed in the gas chamber and configured to detect a specified chemical in the photolyzed exhaust gas sample.

20 Claims, 4 Drawing Sheets

ELECTROCHEMICAL EXHAUST GAS SENSOR WITH PHOTOLYSIS

FIELD

The present disclosure relates to emissions gas detection, and more particularly to electrochemical detection of trace chemicals in exhaust gasses.

BACKGROUND

The statements in this section merely provide background information related to the present disclosure and may not constitute prior art.

Exhaust gas sensors detect chemical species in exhaust gasses of vehicles, such as oxides of nitrogen. The chemical species detected are useful for analysis relative to government regulatory and tailpipe emissions standards. A set of data collected by the sensors may indicate one or more different chemical species, and isolating a specific chemical species present in the exhaust gas may not be conclusively determined from the data alone. Moreover, certain chemical species may cause noise in data that would indicate other chemical species that are more desirable to detect.

The present disclosure addresses these challenges related to detecting chemical species in exhaust gas.

SUMMARY

This section provides a general summary of the disclosure and is not a comprehensive disclosure of its full scope or all of its features.

In one form, a method for detecting a chemical in a gas sample, the method includes collecting the gas sample in a gas chamber of an exhaust gas sensor, photolyzing a background chemical in the gas sample with ultraviolet light transmitted into the gas chamber, and collecting data from an electrochemical sensor, the data indicating an amount of the chemical in the exhaust gas sample.

In variations of the method, which may be implemented individually or in combination: the chemical is nitrogen oxide and the background chemical is nitrogen dioxide; the background chemical is ozone and the detected chemical is at least one of benzene, toluene, and xylene in the gas sample; the detected chemical is formaldehyde; the data include changes in at least one of electrical current or voltage in the electrochemical sensor, the changes in the at least one of electrical current or voltage indicating an amount of the detected chemical present in the gas sample; the method further includes photolyzing the background chemical in the gas sample to reduce noise in the collected data; pulsing the ultraviolet light to photolyze the background chemical; transmitting the ultraviolet light through a fiber optic cable connecting a light source to the gas chamber; collecting the data with an electrolyte sensor element disposed in the gas chamber; the electrolyte sensor element includes an yttria-stabilized zirconia electrolyte.

In another form, an automotive exhaust gas sensor includes a gas chamber, an ultraviolet light source configured to emit ultraviolet light into the gas chamber and to photolyze an exhaust gas sample in the gas chamber, and an electrochemical sensor disposed in the gas chamber and configured to detect a specified chemical in the photolyzed exhaust gas sample.

In variations of the sensor, which may be implemented individually or in combination: the ultraviolet light source is configured to photolyze nitrogen dioxide in the gas sample into nitrogen oxide and to photolyze ozone in the exhaust gas sample into molecular oxygen; the sensor further includes a fiber optic cable having a first end connected to the ultraviolet light source and a second end disposed in the gas chamber, the fiber optic cable configured to transmit the ultraviolet light from the ultraviolet light source to the gas chamber; the specified chemical detected by the electrochemical sensor is at least one of nitrogen oxide, nitrogen dioxide, oxygen or ozone; the specified chemical detected by the electrochemical sensor is at least one of formaldehyde, benzene, toluene, and xylene; the electrochemical sensor includes an yttria-stabilized zirconia electrolyte; the electrochemical sensor includes an electrolyte sensor element in the gas chamber; the electrochemical sensor is configured to transmit data indicating a change in at least one of current or voltage in the electrolyte sensor element, the change in the at least one of current or voltage indicating an amount of the specified chemical in the exhaust gas sample; the ultraviolet light source is configured to emit pulses of the ultraviolet light into the gas chamber; the electrochemical sensor is configured to detect oxygen ions released upon photolysis of a background chemical in the exhaust gas sample.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
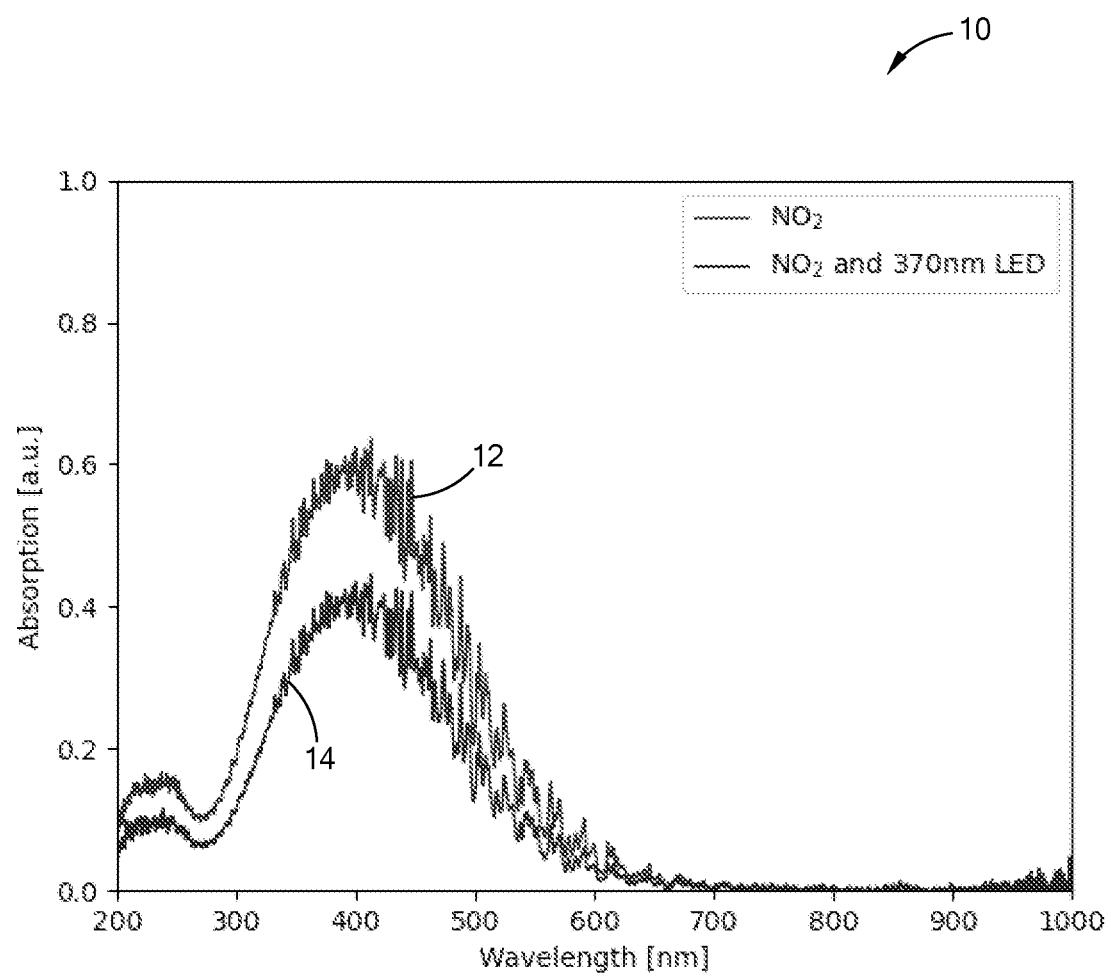
FIG. 1 is a chart of light absorption of a chemical species in an exhaust gas sample according to the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

With reference to FIG. 1, a chemical spectroscopy chart 10 shows plots 12, 14 of optical absorption ranges of light a chemical species in exhaust gas samples. An "optical absorption range" is an amount of light absorbed by a chemical species at a plurality of specified wavelengths of light within a range of wavelengths. A first plot 12 represents light absorption by nitrogen dioxide in a gas sample, and a second plot 14 represents light absorption by nitrogen dioxide in a gas sample photolyzed by ultraviolet light. In the context of this disclosure, a "photolyzed" gas sample is a sample of a gas that has been illuminated with light to photolyze chemicals in the gas, and an "unphotolyzed" gas sample is a sample of a gas that has not been illuminated with light to photolyzed chemicals in the gas. To "photolyze" a gas means to apply light to the gas in order to initiate or augment a chemical reaction that changes molecules of the gas into different molecules. In one form, background nitrogen dioxide ($NO_2$) photolyzes into nitrogen oxide (NO) and monomolecular oxygen (O) when illuminated with ultraviolet light:

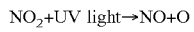

The chart 10 shows an amount of absorption on the vertical axis, measured from 0 to 1 where 0 means no absorption at a specific wavelength of light and 1 means complete absorption of the specific wavelength of light. The chart 10 shows a wavelength of the light on the horizontal axis, measured in nanometers.

The plots 12, 14 of the optical absorption range of the chemical species in the gas sample and the photolyzed gas sample indicate an amount of the chemical species present. That is, a higher value on the chart 10 is interpreted as having more of the chemical species in the sample. The plot 12 of the absorption of nitrogen dioxide in the unphotolyzed gas sample has higher values of absorption than the plot 14 of the absorption of nitrogen dioxide in the photolyzed gas sample. Thus, by illuminating the gas sample to photolyze the nitrogen dioxide, the photolyzed gas sample has less nitrogen dioxide than the unphotolyzed gas sample. The gas sample is illuminated in one form with a light-emitting diode that light in a specified frequency range (e.g., 370 nm) designed to photolyze the nitrogen dioxide. In one form, the specified frequency range is 200-500 nm. A portion of this range is referred to as an "ultraviolet" range because wavelengths of light below 400 nm are shorter than that of visible violet light, and light having wavelengths in this range is "ultraviolet light." Alternatively, a different light source is actuated to emit the ultraviolet light, such as a laser.

In another form, the photolyzed background chemical is ozone ($O_3$) that photolyzes into molecular oxygen ($O_2$) and monoatomic oxygen (O):

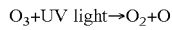

An exhaust gas sensor, such as an electrochemical sensor described below, detects specified chemical species more readily in the photolyzed gas sample than in the unphotolyzed gas sample because the background chemicals reduced by photolysis would otherwise obscure or introduce noise into data collected by the exhaust gas sensor. In one example, the exhaust gas sensor detects the amount of at least one of nitrogen oxide, formaldehyde, benzene, toluene, and xylene in the photolyzed gas sample.

Figure 2:
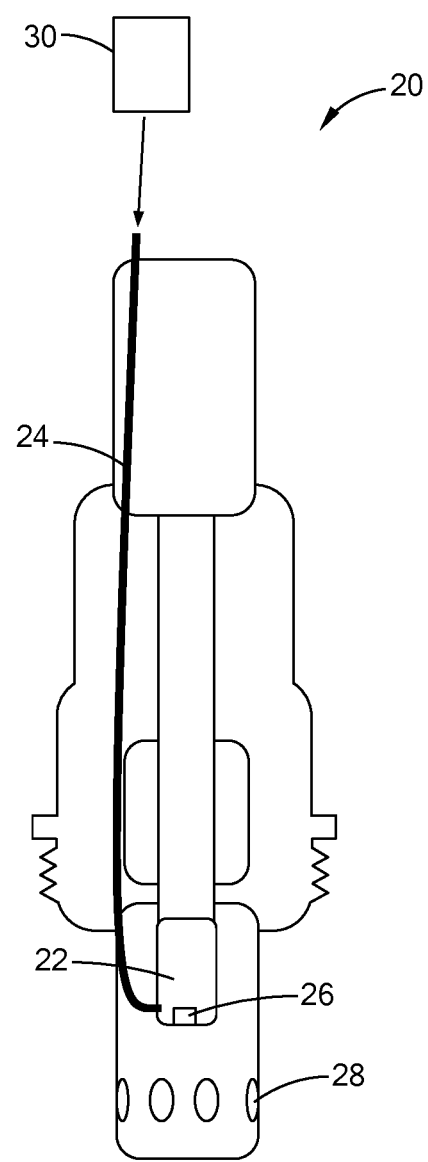
FIG. 2 is a cross-sectional view of an exhaust gas sensor according to the present disclosure.

With reference to FIG. 2, an exhaust gas sensor 20 includes a gas chamber 22, a fiber optic cable 24, an electrochemical sensor 26, and a gas inlet 28. The gas inlet 28 directs exhaust gas from an exhaust pipe to the gas chamber 22, where the fiber optic cable 24 directs light from an external light source 30 to photolyze the exhaust gas. In the form of FIG. 2, the gas inlet 28 is a series of holes in an outer portion of the electrochemical sensor that directs exhaust gas to the entrance of gas chamber 22. The gas chamber 22 may include multiple internal, gas-permeable, diffusion-limited partitions, as well as a diffusion-limited pathway at its entrance. The electrochemical sensor 26 includes an electrolyte sensing element in the gas chamber 22 that provides data indicating the presence of specific chemical species in the photolyzed gas. When the gas chamber 22 includes multiple partitions, each internal chamber may include an individual electrolyte sensing element.

As described above, the exhaust gas sensor 20 detects specific chemical species in the photolyzed gas that would otherwise be obscured by background chemicals such as nitrogen dioxide and ozone.

The exhaust gas sensor 20 detects chemical species in the gas based on data collected with the electrochemical sensor 26 disposed in the gas chamber 22. Electrons and ions from specific chemical species in the exhaust gas cause changes in the electrical current or voltage in the electrolyte sensing element of the electrochemical sensor 26, and data indicating these current or voltage changes is sent to a controller, such as a controller 32 described in greater detail below. In one form, the electrochemical sensor 26 is configured to detect oxygen ions (such as monoatomic oxygen described above) released upon photolysis of a background chemical such as nitrogen dioxide or ozone. In another form, the electrochemical sensor 26 is configured to detect diatomic oxygen, which forms upon recombination of monoatomic oxygen that is released upon photolysis of a background chemical such as nitrogen dioxide or ozone. In another form, the electrochemical sensor 26 is configured to detect oxygen that is electrochemically separated from oxides of nitrogen, whose relative concentration is altered upon photolysis of a background chemical such as nitrogen dioxide or ozone. In each of these examples, the presence of exhaust gas in gas chamber 22 produces a changed electrical current or voltage in the electrochemical sensor 26. The specific changes in the electrical current or voltage are correlated to amount of specific chemicals in the exhaust gas. The controller thus determines amounts of specific chemical species in the photolyzed gas based on the changes of the electric current or voltage in the electrochemical sensor 26. The data indicate an amount of nitrogen dioxide and an amount nitrogen oxide in the photolyzed gas, allowing the electrochemical sensor 26 to differentiate between nitrogen dioxide and nitrogen oxide. The data further indicate respective amounts of at least one of diatomic oxygen, ozone, formaldehyde, benzene, toluene, and xylene in the photolyzed gas. Background chemical species such as nitrogen dioxide and ozone may cause similar electric current changes to those caused by chemical species that are desirable to detect, such as nitrogen oxide, formaldehyde, benzene, toluene, and xylene. Because the background chemical species are photolyzed, noise in the data collected by the electrochemical sensor 26 is reduced. By photolyzing the gas sample to reduce amounts of the background chemicals, the desired chemical species are more easily detected by the exhaust gas sensor 20. In one form, the electrolyte sensor element of the electrochemical sensor 26 includes an yttria-stabilized zirconia electrolyte.

The fiber optic cable 24 transmits ultraviolet light from the light source 30, such as a light-emitting diode, to the gas chamber 22. In the form of FIG. 2, the fiber optic cable 24 extends along an interior of the electrochemical sensor 26 to an end disposed in the gas chamber 22. In another form not shown in the figures, the fiber optic cable 24 is disposed on an exterior of the exhaust gas sensor 20. The ultraviolet light transmitted through the fiber optic cable 24 photolyzes the nitrogen dioxide and the ozone in the exhaust gas. In one form, the light source 30 transmits a continuous amount of ultraviolet light through the fiber optic cable. In another form, the light source 30 pulses the ultraviolet light, i.e., emits the light in periodic bursts punctuated by periods without light, to photolyze the gas sample. By pulsing the ultraviolet light, the data collected by the electrolyte sensor element are correlated to the timing of the periodic pulsing of the light source 30, indicating time periods when chemical species such as nitrogen dioxide in the exhaust gas are photolyzed.

Figure 3:
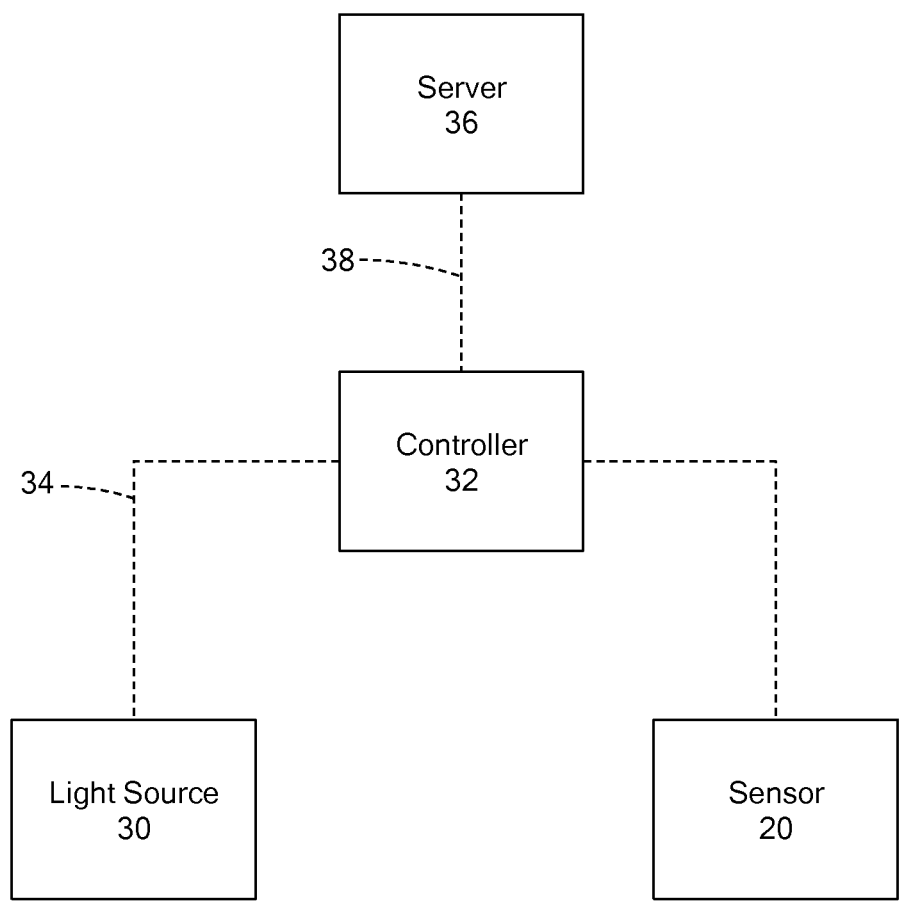
FIG. 3 is a block diagram of a controller that operates the exhaust gas sensor according to the present disclosure.

With reference to FIG. 3, a controller 32 controls the light source 30 and the exhaust gas sensor 20 to collect data about chemicals in the exhaust gas sample. The controller 32 provides instructions to the light source 30 to emit light to photolyze the gas sample. The controller 32 collects data from the exhaust gas sensor 20, such as current or voltage data from the electrochemical sensor 26. The controller 32 is configured to determine chemical species in the exhaust gas sample based on the data received from the exhaust gas sensor 20. In one form, the controller compares real-time current or voltage data collected by the electrochemical sensor 26 over a span of time to stored current or voltage signatures for specified chemical species. In another form, the controller compares current or voltage data collected by the electrochemical sensor 26 with and without active photolysis. Based on the comparison, the detection algorithm determines an amount of the specified chemical species in the exhaust gas sample. In another form, the electrochemical sensor 26 utilizes phase sensitive detection synchronized with the frequency of pulsed ultraviolet light. In one form, one or more running averages or running integrations of real-time current or voltage data after multiplication are taken with reference sine, cosine, square, or other periodic wave functions. The output of the running averages or integrations is then filtered to include current or voltage data at the frequency of the photolysis pulse frequency, with a magnitude proportional to the difference induced by photolysis. Photolyzing the gas sample reduces background chemical species that the electrochemical sensor 26 is sensitive to detect, allowing detection of other trace species such as formaldehyde, benzene, toluene, and xylene. This results in improved chemical selectivity and sensitivity in the output of the electrochemical sensor 26.

The controller 32 communicates with the light source 30 and the exhaust gas sensor 20 via a communications path 34, such as a bus, a wired network, or a wireless network. The controller 32 stores the collected chemical species data in a memory. In one form, the controller 32 transmits the collected data to an external server 36 via a wireless communications path 38 that tracks chemical emissions data from a plurality of vehicles. The controller 32 is housed in the vehicle.

Figure 4:
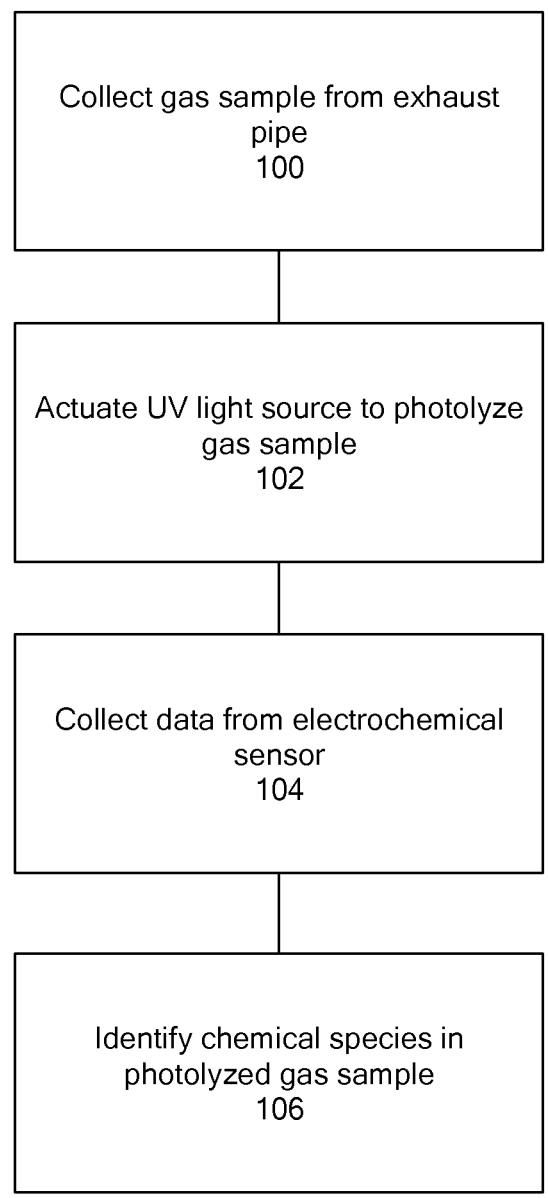
FIG. 4 is a block diagram of a process for detecting chemical species in the exhaust gas sample with the exhaust gas sensor according to the present disclosure.

FIG. 4 is a block diagram of an example process for detecting specific chemicals in a photolyzed exhaust gas sample. The process begins in a block 100, in which a gas sample is collected from an exhaust pipe of a vehicle. An exhaust gas sensor 20, such as shown in FIG. 2 above, is disposed in the exhaust pipe to collect the gas sample. The gas sample is collected via a gas inlet 28 of the exhaust gas sensor 20 that directs the gas sample to a gas chamber 22.

Next, in a block 102, a controller 32, such as is shown in FIG. 3, actuates an ultraviolet light source 30 to photolyze the gas sample. As described above, photolyzing the gas sample reduces respective amounts of background chemicals such as nitrogen dioxide and ozone, allowing other chemical species to be detected by the exhaust gas sensor 20, such as formaldehyde, benzene, toluene, and xylene. The ultraviolet light source 30 in one form is a light-emitting diode configured to emit light having a wavelength of 370 nm.

Next, in a block 104, the controller 32 collects data from an electrochemical sensor 26 of the exhaust gas sensor 20. As described above, an electrolyte sensor element of the electrochemical sensor 26 measures changes to electrical current or voltage caused by the gasses in the gas sample. Because the background chemical species are photolyzed, noise in the data collected by the electrochemical sensor 26 is reduced. The electrochemical sensor 26 transmits data indicating the current changes to the controller 32 via a communications path 34.

Next, in a block 106, the controller 32 identifies amounts of one or more chemical species in the photolyzed gas sample. As described above, chemicals have specific electric current or voltage changes that may be similar with electric current or voltage changes of the background chemicals. By reducing the amounts of the background chemicals, the specified chemicals are more easily detected. The controller 32 stores data indicating the amounts of the specified chemical species in a memory module. Following the block 106, the process ends.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, material, manufacturing, and assembly tolerances, and testing capability.

As used herein, the phrase at least one of A, B, and C should be construed to mean a logical (A OR B OR C), using a non-exclusive logical OR, and should not be construed to mean "at least one of A, at least one of B, and at least one of C."

In this application, the term "controller" and/or "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The term memory is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A method for detecting a chemical in a gas sample, the method comprising:
   collecting the gas sample in a gas chamber of an exhaust gas sensor;
   photolyzing a background chemical in the gas sample with ultraviolet light transmitted into the gas chamber; and
   collecting data from an electrochemical sensor of the exhaust gas sensor, the data indicating an amount of the chemical in the exhaust gas sample.

2. The method of claim 1, wherein the chemical is nitrogen oxide and the background chemical is nitrogen dioxide.

3. The method of claim 1, wherein the background chemical is ozone and the detected chemical is at least one of benzene, toluene, and xylene in the gas sample.

4. The method of claim 1, wherein the detected chemical is formaldehyde.

5. The method of claim 1, wherein the data include changes in at least one of electrical current or voltage in the electrochemical sensor, the changes in the at least one of electrical current or voltage indicating an amount of the detected chemical present in the gas sample.

6. The method of claim 5, further comprising photolyzing the background chemical in the gas sample to reduce noise in the collected data.

7. The method of claim 1, further comprising pulsing the ultraviolet light to photolyze the background chemical.

8. The method of claim 1, further comprising transmitting the ultraviolet light through a fiber optic cable connecting a light source to the gas chamber.

9. The method of claim 1, further comprising collecting the data with an electrolyte sensor element disposed in the gas chamber.

10. The method of claim 9, wherein the electrolyte sensor element includes an yttria-stabilized zirconia electrolyte.

11. An automotive exhaust gas sensor, comprising:
    a gas chamber;
    an ultraviolet light source configured to emit ultraviolet light into the gas chamber and to photolyze an exhaust gas sample in the gas chamber; and
    an electrochemical sensor disposed in the gas chamber and configured to detect a specified chemical in the photolyzed exhaust gas sample.

12. The sensor of claim 11, wherein the ultraviolet light source is configured to photolyze nitrogen dioxide in the gas sample into nitrogen oxide and to photolyze ozone in the exhaust gas sample into molecular oxygen.

13. The sensor of claim 11, further comprising a fiber optic cable having a first end connected to the ultraviolet light source and a second end disposed in the gas chamber, the fiber optic cable configured to transmit the ultraviolet light from the ultraviolet light source to the gas chamber.

14. The sensor of claim 11, wherein the specified chemical detected by the electrochemical sensor is at least one of nitrogen oxide, nitrogen dioxide, oxygen or ozone.

15. The sensor of claim 11, wherein the specified chemical detected by the electrochemical sensor is at least one of formaldehyde, benzene, toluene, and xylene.

16. The sensor of claim 11, wherein the electrochemical sensor includes an yttria-stabilized zirconia electrolyte.

17. The sensor of claim 11, wherein the electrochemical sensor includes an electrolyte sensor element in the gas chamber.

18. The sensor of claim 17, wherein the electrochemical sensor is configured to transmit data indicating a change in at least one of current or voltage in the electrolyte sensor element, the change in the at least one of current or voltage indicating an amount of the specified chemical in the exhaust gas sample.

19. The sensor of claim 11, wherein the ultraviolet light source is configured to emit pulses of the ultraviolet light into the gas chamber.

20. The sensor of claim 11, wherein the electrochemical sensor is configured to detect oxygen ions released upon photolysis of a background chemical in the exhaust gas sample.

* * * * *